United States Patent
Bau-Madsen et al.

(10) Patent No.: US 9,201,059 B2
(45) Date of Patent: Dec. 1, 2015

(54) MICROFLUIDIC SYSTEM AND A METHOD OF PERFORMING A TEST

(75) Inventors: Niels Kristian Bau-Madsen, Hellerup (DK); Jacques Jonsmann, Gorlose (DK); Bent Overby, Glostrup (DK); Christianus Berendsen, Soborg (DK)

(73) Assignee: SCANDINAVIAN MICRO BIODEVICES APS, Farum (DK)

( * ) Notice: Subject to any disclaimer, the term of this patent is extended or adjusted under 35 U.S.C. 154(b) by 667 days.

(21) Appl. No.: 12/922,573

(22) PCT Filed: Mar. 13, 2009

(86) PCT No.: PCT/DK2009/050058
§ 371 (c)(1),
(2), (4) Date: Nov. 3, 2010

(87) PCT Pub. No.: WO2009/112038
PCT Pub. Date: Sep. 17, 2009

(65) Prior Publication Data
US 2011/0045492 A1 Feb. 24, 2011

(30) Foreign Application Priority Data
Mar. 14, 2008 (DK) .................................. 2008 00401

(51) Int. Cl.
*B01L 3/00* (2006.01)
*G01N 33/49* (2006.01)
(Continued)

(52) U.S. Cl.
CPC .......... *G01N 33/4905* (2013.01); *B01L 3/5027* (2013.01); *G01N 33/5304* (2013.01);
(Continued)

(58) Field of Classification Search
CPC .......... B01L 3/5027; B01L 2300/0883; G01N 33/4905; G01N 33/5304; G01N 33/86
See application file for complete search history.

(56) References Cited

U.S. PATENT DOCUMENTS

| 4,034,601 A | 7/1977 | Geiger |
| 5,144,139 A | 9/1992 | Hillman et al. |

(Continued)

FOREIGN PATENT DOCUMENTS

| WO | WO 99/64840 A1 | 12/1999 |
| WO | WO 2004/042402 A2 | 5/2004 |

(Continued)

OTHER PUBLICATIONS

International Search Report (PCT/ISA/210) issued on Oct. 30, 2009, by the European Patent Office as the International Searching Authority for International Application No. PCT/DK2009/050058.
(Continued)

*Primary Examiner* — Melanie Y Brown
(74) *Attorney, Agent, or Firm* — Buchanan Ingersoll & Rooney PC

(57) ABSTRACT

The invention relates to a microfluidic system comprising a microfluidic device having a first and a second opposite surfaces and an optical detector, the microfluidic device comprises a flow channel with a detection channel section having a length of at least about 1 mm, the microfluidic device comprises at least one aperture section comprising at least a part of said detection channel section and a transparent window into said detection channel section, the optical detector is arranged to determine at least one optical property of said aperture section as a function of time. The flow channel may have capillary dimensions and/or it may wholly or fully be arranged to drive a fluid flow by applying external forces. The microfluid device may be used to determine various properties of a sample fluid, for example it may be used to determine a samples coagulation properties and/or reactions of one or more components in a fluid sample as a function of time.

44 Claims, 5 Drawing Sheets

(51) Int. Cl.
*G01N 33/53* (2006.01)
*G01N 33/86* (2006.01)

(52) U.S. Cl.
CPC ......... *G01N33/86* (2013.01); *B01L 2200/0684* (2013.01); *B01L 2200/148* (2013.01); *B01L 2300/0654* (2013.01); *B01L 2300/0883* (2013.01); *B01L 2300/18* (2013.01); *B01L 2400/0406* (2013.01); *B01L 2400/0487* (2013.01)

(56) References Cited

U.S. PATENT DOCUMENTS

| | | |
|---|---|---|
| 5,167,145 A | 12/1992 | Butler et al. |
| 5,300,779 A | 4/1994 | Hillman et al. |
| 5,372,948 A * | 12/1994 | Yip ............................... 436/534 |
| 5,534,226 A | 7/1996 | Gavin et al. |
| 5,569,608 A | 10/1996 | Sommer |
| 6,221,226 B1 * | 4/2001 | Kopf-Sill ....................... 204/602 |
| 6,488,896 B2 | 12/2002 | Weigl et al. |
| 6,766,187 B1 * | 7/2004 | Black et al. .................... 600/473 |
| 2002/0076354 A1 * | 6/2002 | Cohen ............................. 422/72 |
| 2002/0110922 A1 | 8/2002 | Shartle et al. |
| 2003/0054558 A1 | 3/2003 | Kurabayashi et al. |
| 2003/0087300 A1 * | 5/2003 | Knapp et al. ....................... 435/6 |
| 2003/0096328 A1 * | 5/2003 | Smith et al. .................. 435/7.23 |
| 2003/0215863 A1 * | 11/2003 | Chow et al. ....................... 435/6 |
| 2004/0011975 A1 | 1/2004 | Nicoli et al. |
| 2004/0206399 A1 | 10/2004 | Heller et al. |
| 2004/0265172 A1 | 12/2004 | Pugia et al. |
| 2005/0243304 A1 | 11/2005 | Padmanabhan et al. |
| 2006/0246575 A1 | 11/2006 | Lancaster et al. |
| 2010/0089529 A1 | 4/2010 | Barholm-Hansen et al. |
| 2010/0167318 A1 * | 7/2010 | Linder ......................... 435/7.92 |
| 2011/0315229 A1 * | 12/2011 | Linder et al. ...................... 137/1 |

FOREIGN PATENT DOCUMENTS

| | | |
|---|---|---|
| WO | WO 2004/044560 A1 | 5/2004 |
| WO | WO 2006/042332 A2 | 4/2006 |
| WO | WO 2006/074665 A2 | 7/2006 |

OTHER PUBLICATIONS

Written Opinion (PCT/ISA/237) issued on Oct. 30, 2009, by the European Patent Office as the International Searching Authority for International Application No. PCT/DK2009/050058.

\* cited by examiner

MICROFLUIDIC SYSTEM AND A METHOD OF PERFORMING A TEST

TECHNICAL FIELD

The invention relates to a microfluidic system for use in test of a biological fluid sample, such as blood where a fluid sample undergoes a reaction such as a coagulation reaction or an agglutination reaction. The invention also relates to a method of performing such test.

BACKGROUND ART

Microfluidic devices and systems for performing blood tests and tests on other types of biological fluids are widely known and are used for performing tests of different types, such a coagulation tests e.g. for determining the coagulation rate in a blood sample or agglutination tests e.g. for determining blood type of a blood sample.

Devices and systems for performing blood tests using an optical detector for determining a change in the blood sample due to a reaction with a reagent. Such systems and methods for performing optically based blood tests are e.g. disclosed in U.S. Pat. No. 4,034,601 (American Hospital Supply), which discloses a method and apparatus for measuring coagulation on blood on a filament. A filament strip is drawn through a blood sample mixed with a clotting reagent until a clot is detected. The coagulation time until clotting is optically measured.

U.S. Pat. No. 5,167,145 (David M Butler et al.) describes a method recording the clotting time of whole blood as it proceeds from fibrinogen through known stages of coagulation, culminating in the cross-linking of the fibrin clot which ultimately solidifies and dries at the end of a cycle, including the steps of:

providing a measured sample of whole blood to be tested;
  transmitting infrared electromagnetic energy through the blood sample;
  detecting the transmission of the infrared energy and electronically producing the signals in response to said infrared energy; and
  measuring a peak transmission level of said infrared energy and calibrating said peak signal in terms of clotting time of said whole blood sample whereby the clotting time is represented by the peak transmission level of the infrared energy through the whole blood sample.

US 2002/0110922 (Bozicevic) describes a method of recording the clotting time of whole blood in a fluid device. Blood is introduced in the flow device, react with a coagulation reagents, and proceed to fill a measuring chamber where flow is stopped by a stop junction. Formation of a blood clot is measuring using an optical detector—blood clotting result in reduction of transmission. A similar method is described in WO 2004/044560.

U.S. Pat. No. 6,488,896 describes a method and a microfluidic device to determine optically if any agglutination and or coagulation take place or not. Time for the reaction is not measured.

U.S. Pat. No. 5,534,226 (International Technidyne) describes a method and a micruflidic device to determine if any agglutination and or coagulation takes place the time is measured by measuring its presents in specific zones and by using CPU chip linked to a timer (clock)

WO 2006/042332 (FASTRAQ) describes a method and a microfluidic device for performing a immobilization test on a biological fluid such as blood or urine. The device is arranged for controlling flow rate to adjust incubation time. Optical means may be used for detecting progress of events, such as sample introduction.

The prior art devices and methods for testing fluid samples using an optical detector basically determine a change in the fluid sample by a corresponding change in light absorbance/reflection at certain wavelength.

DESCRIPTION OF INVENTION

The object of the present invention is to provide a novel microfluidic system and as well a method of performing a test of a biological fluid sample which method is very reliable, simple to perform, very fast and economically feasible.

This object has been achieved by the invention as it is defined in the claims.

As it will be clear from the following description, embodiments of the invention achieve other objectives and have other desired and beneficial effects.

The microfluidic system of the invention comprises a microfluidic device having a first and a second opposite surfaces and an optical detector.

The microfluid system is in the following described with one optical detector, but as it will be understood by the skilled person the microfluid system could comprise two or more optical detectors.

The microfluid device may in one embodiment be essentially planar. In general a planar microfluid device is simpler to produce than a non-planar microfluid device. However, for the function the microfluid device need not be planar. A planar microfluid device is a microfluid device with essentially plane first and second surfaces, which preferably may be equidistant to each other.

The microfluidic device comprises at least one flow channel. In general the microfluid device is described with one flow channel, but it should be understood that the microfluid device may have as many flow channel as desired, where at least one flow channel is as defined in the claims and described herein.

The term microfluid device means that the device comprises at least one flow channel which has at least one cross-sectional dimension in the micro range i.e. less than about 1000 μm.

The microfluidic device comprises a flow channel with a detection channel section. The detection channel section is defined as the section of the flow channel which is arranged to be subjected to an optical detection and which is within or is arranged to be within an aperture section for performing a desired optical detection. Accordingly the microfluid device comprises an aperture section comprising at least a part of said detection channel section and a transparent window into said detection channel section. The aperture section is the section of the microfluid device onto which the optical detection is performed. The optical detector is arranged to be in optical communication with said aperture section to determining at least one optical property of said aperture section as a function of time.

It should be understood that the microfluid device may comprise two or more aperture sections.

The aperture section may accordingly change e.g. if the beam size of the optical detector is changed or the distance between the microfluid device and the optical detector is changed. In one embodiment the microfluidic system is arranged such that the one or more aperture sections are or can be kept essentially constant. In another embodiment the one or more aperture sections are changed or moved according to a pre-selected scheme.

In general the optical detector is arranged to transmit light onto at least the whole of the aperture section(s) and to detect changes of an optical property from the whole of the aperture section(s).

The aperture section(s) comprises accordingly at least a part of at least one detection channel section, but may also comprise an area surrounding the detection channel section(s), in particular if the detection channel section(s) is not straight. Such area surrounding said detection channel section(s) in the aperture is also referred to as the aperture area. In most situation the aperture section will comprises at least a part of one or more detection channel sections and an aperture area, where the at least one optical property of the area surrounding said detection channel section(s), is kept essentially constant, such that any change in optical property detected in the aperture section can be ascribed to a change in optical property of said detection channel section(s).

In one embodiment the aperture section comprises all of said detection channel section. In one embodiment where the aperture section is movable the aperture section can be moved to cover all of said detection channel section. In one embodiment where there are two or more apertures the two or more apertures in total comprises all of said detection channel section.

In one embodiment the aperture section comprises at least a part of said detection channel section and an aperture area beyond said detection channel section, the aperture area beyond said detection channel sections being transparent.

In one embodiment the aperture section comprises at least a part of said detection channel section and an aperture area beyond said detection channel section, the aperture area beyond said detection channel section being essentially non-transparent, the aperture area beyond said detection channel section preferably being absorbing and/or reflecting light from said optical detector.

The aperture section may in principle have any size which is sufficient to obtain a measurement, such as at least about 10 $\mu m^2$, such as between about 100 $\mu m^2$ and about 10 $cm^2$, such as between about 1 $mm^2$ and about 200 $mm^2$ depending on the length and with of the detection channel.

In one embodiment the aperture section or the aperture sections in total preferably cover a size of at least about 10 $\mu m^2$, such as between about 100 $\mu m^2$ and about 10 $cm^2$, such as between about 1 $mm^2$ and about 200 $mm^2$.

Most preferably the aperture area is absorbing the major amount of the light from the optical device. Thereby the risk of measuring errors is highly reduced. The absorbing aperture area may be provided by incorporating an absorbing ink in the microfluid device in the area outside the window(s).

In one embodiment the microfluidic device is provided from at least 2 transparent parts at least one of them having a groove for providing the flow channel, the at least two parts are fixed to each other in a interface, the interface comprises an absorbing material, which is less transparent than the 2 transparent parts, the absorbing material e.g. an ink, preferably being essentially non-transparent to light used by the optical detector.

The microfluidic device comprises an inlet for feeding a fluid sample, and an air escape opening for allowing air to escape as the channel is filled with the sample. Any arrangement and shapes of inlets and air escape openings may be provided.

The length of the detection channel section is the length along the flow direction of the flow channel. The length may be measured as the length along the center axis of the flow channel.

The term 'transparent window' means that a measurable amount of light used by the optical detector can pass through the window to the flow channel or a medium in the flow channel.

The detection channel section should preferably have a length which is sufficient for the sample to flow into e.g. the length should normally be at least about 1 mm in length. Often it is desired for obtaining a stable floe that the length of the detection channel in about 10 mm, since it in practice may be difficult to perform a reliable detection if the detection channel section is substantially shorter. In one embodiment the detection channel section has a length of at least about 60 mm, such as at least about 100 mm, such as at least about 200 mm, such as at least about 500 mm, such as at least about 1000 mm, such as between about 100 and about 50000 mm, such as between about 100 and about 2000 mm.

The length of the detection channel section may preferably be selected in accordance with the detection to be performed, such that given the expected flow velocity of a selected fluid sample in a selected test, the optical property measured or a pressure/suction regulated in accordance to said optical property is expected to change as a function of time in the time-frame where the fluid sample is expected to have a flow front in the detection channel section.

In one embodiment the flow channel comprises two or more detection channel sections which may preferably be arranged is said aperture section (or in an alternative embodiment in two separate aperture sections). Preferably at least one of said detection channel sections is significant longer than the one or more other detection channel sections, such as at least about 25% longer, such as at least about 100% longer, such as at least 500% longer. In this embodiment the first (seen in flow direction) detection channel section is used to set a time where the flow is at a specific starting point, and the second (seen in flow direction) detection channel section is used to determining at least one optical property of said aperture section as a function of time.

As mentioned the detection channel section may be straight, but since it is simpler to obtain high quality and reliable result when the detection channel section has a relatively long length, it is desirable to provide the detection channel section with one or more curves. In one embodiment the detection channel section therefore comprises one or more bended curves. The detection channel section may in principle be bended to have any shape. In one embodiment the detection channel section is arranged to comprise coiled curves, double coiled curves and/or meander shaped curves, preferably the detection channel section is arranged to have meander shape comprising a plurality of parallel sections connected to each other with curved sections. Additional desired shapes of the detection channel section are shown in the figures.

In one embodiment only a part of the flow channel comprises a transparent window, this part of the flow channel includes at least the detection channel section. In one embodiment where only a part of the flow channel comprises a transparent window, this part of the flow channel constitutes the detection channel section.

In one embodiment the device comprises a transparent window into said flow channel section beyond the detection channel section. Preferably the device comprise a transparent window into the flow channel in essentially its entire length.

The transparent window into said detection channel section may be provided by a transparent wall section between the detection channel section and the first surface of the microfluidic device. This wall section is usually called the top wall.

In one embodiment the detection channel section has a second transparent window along its length provided by a wall section between the detection channel section and the second surface of the microfluidic device. This wall section is usually called the bottom wall. In this embodiment the detection channel section is transparent at least in the absence of fluids or solids in the detection channel section, i.e. light can pass through the detection channel section at least in the absence of fluids or solids in the detection channel section.

The detection channel section of the flow channel may in principle have any dimension, preferably having at least one dimension of about 10000 µm or below, such as at least one dimension of about 1000 µm or below, such as at least one dimension of about 500 µm or below.

In one preferred embodiment the detection channel section of the flow channel or at least a part thereof has capillary dimensions.

The term 'capillary dimension' means that the dimension and surface characteristics of the channel are selected such that a capillary pull is applied to a fluid sample in the channel.

By surface characteristics is meant surface ability to be wetted by the fluid sample. The tension(s) at various part of the surface is often decisive for the wettability of the sample The surface tension may e.g. be regulated using any method for example the method disclosed in any one of US 2004/0206399, US 2004/0265172 and DK PA 2005 00732.

The surface tension may be measured using a tensiometer, such as a SVT 20, Spinning drop video tensiometer marketed by DataPhysics Instruments GmbH. In this application the terms "surface tension" designate the macroscopic surface energy, i.e. it is directly proportional to the hydrophilic character of a surface measured by contact angle to water.

The decisive dimension of the channel is often the smallest cross-sectional dimension.

As a fluid flow front is progressing through a flow channel it has to overcome the resistance provided by the surface in particular in order to wet the surface. The capillary forces should be larger than the surface resistance in order for the fluid flow front to progress through the flow channel by capillary forces. If the capillary forces is insufficient external forces in the form of pressure applied upstream or suction applied downstream or both may be applied In one embodiment the detection channel section does not have capillary dimensions, the microfluidic device comprises an external pressure or suction source for driving a liquid flow in the detection channel section.

In one embodiment the microfluidic device comprises an external pressure and/or suction source for driving a liquid flow in the detection channel section, the external pressure and/or suction source preferably being controllable, optionally to provide an essentially constant pressure or suction force or to provide a gradually increasing pressure or suction force.

In one embodiment the microfluidic device comprises an external pressure and/or suction source for driving a liquid flow in the detection channel section, the external pressure and/or suction source being connected to the optical detector so as to adjust the progress of the flow front of a liquid sample to a desired constant or varying velocity. The optical detector may thereby be used to provide a feed back value to the external pressure and/or suction source. The applied pressure/suction may preferably be used to determine if, when, and/or to which degree a reaction of one or more component in the fluid sample have taken place within the detection channel section. In one embodiment the pressure and/or suction source may be arranged to provide a back flow of the fluid sample. In one embodiment the pressure/suction is applied such that the flow direction is switching repeatably between ordinary forward flow and back flow, and the optical detector is measuring the reaction of the fluid over time as a function of the pressure/suction applied.

In one embodiment the detection channel section of the flow channel has capillary dimensions for a biological sample comprising at least about 10% by volume of biological fluid, such as at least about 40% by volume of biological fluid, such as between about 50% and essentially about 100% by volume of biological fluid, the remaining part of the biological sample preferably being selected from water, physiologically aqueous solution and reagent for the biological fluid.

The water, physiologically aqueous solution and/or reagent for the biological fluid may be added prior to feeding the fluid sample to the inlet of the flow channel or it may be added within the flow channel.

The term 'biological fluid' means fluid selected from a fluid as sampled directly from an animal or a human, a mixture of fluids as sampled directly from an animal or a human, one or more fractions of fluid as sampled directly from an animal or a human, and reconstructed and artificial fluid resembling one or more animal and/or human fluids or fractions thereof.

In one embodiment the detection channel section of the flow channel has capillary dimensions for a biological sample comprising a biological fluid selected from the group of blood fractions, whole blood, urine and saliva.

In one embodiment the detection channel section of the flow channel has capillary dimensions for a biological sample comprising at least about 90% by volume of whole blood.

In one embodiment the detection channel section of the flow channel along its whole length has a smallest cross-sectional dimension of about 1000 µm or less, such a of about 500 µm or less such as from about 10 µm to about 250 µm, such as from about 50 µm to about 200 µm. In situation where the flow channel need not having capillary dimension the smallest cross-sectional dimension may e.g. be between about 200 and about 5000 µm, such as between about 500 and about 1000 µm.

In one embodiment wherein the detection channel section has a bottom surface and a top surface, the distance between the bottom surface and the top surface is of capillary dimension, preferably the distance between the bottom surface and the top surface is about 1000 µm or less, such a of about 500 µm or less such as from about 10 µm to about 250 µm, such as from about 50 µm to about 200 µm.

The distance between the bottom surface and the top surface may be essentially constant or it may vary. It is in general desired that the distance between the bottom surface and the top surface may be essentially constant because a change due to a reaction in the sample is simpler to determine when the position of the fluid flow front need not to be taken into consideration. However, the distance between the bottom surface and the top surface may vary provided that the variation in function of the length of the detection channel section is known to the user.

The flow channel has a channel depth which may be equal or may vary along its length where the depth (also called the cross sectional depth) in a cross sectional cut of the flow channel is measured as the largest dimension perpendicular to the first surface of the flow channel in said cross sectional cut.

The flow channel has a channel width which may be equal or may vary along its length where the width (also called the cross sectional width) in a cross sectional cut of the flow channel is measured as the largest dimension parallel to the first surface of the flow channel in said cross sectional cut.

In one embodiment the channel width being essentially constant along the major length of the detection channel section, such as at least about 70% of the length of the detection channel section, such as at least about 80% of the length of the detection channel section, such as the whole length of the detection channel section.

In one embodiment the detection channel section comprises at least one position indicator provided by an abrupt change of the channel width. The abrupt change of the channel width preferably being at least about a 25% change of width, such as at least about a 50% change of width, such as at least about a 100% change of width within a length of channel of about 5 mm. Alternatively or additionally a position indicator may be provided by, an abrupt change in surface tension of at least a part of the surface in the channel and an abrupt change in aperture transparence in the detection channel section.

The abrupt change of the channel width may in one embodiment comprise a sharp edged change which may result in a geometrical barrier to the fluid sample. The geometrical barrier may e.g. be such at to provide a local time delay. The geometrical barrier may e.g. be overcome by a capillary pull after such local time delay and/or an external pressure/suction may be applied.

In one embodiment the abrupt change of the channel width have rounded edge(s) so as to avoid forming a geometrical barrier to the fluid sample.

In order to provide that a given volume of fluid sample in the flow front of the sample result in a change of an optical property of the aperture section which is as large as possibly the cross sectional channel area of the position indicator should preferably not be too much larger than the cross sectional channel area of the detection channel section beyond the position indicator.

In one embodiment the detection channel section has a cross-sectional channel area parallel to the first surface, the cross-sectional channel area changes less, such as at least about 25% less, such as at least about 50% less, such as at least about 75% less in percentage than the percentage change of channel width along said position indicator, preferably the cross-sectional channel area is essentially constant along said position indicator.

In order to decrease the cross-sectional channel area in said position indicator the detection channel section in one embodiment comprises one or more protruding elements along at least a part of said position indicator, the protruding elements preferably being protruding from a bottom of the flow channel towards the first surface, the protruding elements preferably being in the form of one or more flanges aligned in the length direction of the flow channel to provide as little flow resistance as possibly. The one or more protruding elements may have a relatively high surface tension and preferably be arranged such as to provide a capillary pull in the flow front of the fluid sample.

In practice the microfluid device may comprise one or more position indicator which in principle may be placed any where in the detection channel section where it is desired to have information about if and/or when this position has been reached by the flow front of a fluid sample.

In one embodiment the detection channel section comprises a position indicator immediately adjacent to a part of the flow channel which is upstream to or downstream to the aperture section.

The term 'upstream' means before as seen in the flow direction of a fluid sample in the microfluidic device. Accordingly the term 'downstream' means after as seen in the flow direction of a fluid sample in the microfluidic device In one embodiment the detection channel section comprises a position indicator immediately adjacent to a reaction chamber, preferably immediately upstream to a reaction chamber.

In one embodiment the flow channel comprises one or more chambers in the form of channel sections having more than about 50% larger cross sectional area in a sectional cut perpendicular to the centre direction of the flow channel, said chambers may e.g. be arranged to be used as reservoir chambers, mixing chambers, reaction chambers, incubation chambers, and termination chambers.

Such chambers may have any size and shape as it is well known in the art, e.g. as disclosed in U.S. Pat. No. 5,300,779 and U.S. Pat. No. 5,144,139.

In one embodiment the micro fluidic device has 2, 3, 4 or even further chambers of equal or different size.

In one embodiment the flow channel comprises at least one reaction chamber, the reaction chamber preferably being placed upstream to the detection channel section, or in the detection channel section. The fluid sample may be subjected to a reagent in said reaction chamber.

In one embodiment the reaction chamber preferably being placed immediately upstream to the detection channel section, thereby the fluid sample may be subjected to a reagent in said reaction chamber immediately prior to enter the detection channel section.

In one embodiment the detection channel section comprises a reaction chamber with a reagent, where the reagent in non dissolved condition has an optical property which differs when the reagent is dissolved. Thereby it will be possibly optically to detect if and optionally when the reagent is dissolved in the fluid sample. This feature can be used to certify that a test has been performed according to a given test scheme.

The reagent in the reaction chamber may be any reagent for the fluid sample. The skilled person knows such reagents for selected fluid samples.

In one embodiment the reaction chamber comprises an agglutination reagent or a coagulation reagent for a fluid sample.

In one embodiment the detection channel section of the flow channel is essentially free of biochemical components, preferably the detection channel section of the flow channel is essentially free of immobilized capture probes, such as immobilized capture agent selected from the group consisting of antibodies, antigens, polypeptides, enzymes, nucleic acids, such double stranded, partly single stranded and single stranded DNA, RNA, LNA and PNA.

The term that the detection channel section of the flow channel be essentially free of biochemical components, means that the detection channel section of the flow channel should not comprise biochemical components prior to use i.e. prior to feeding the sample to the microfluidic device. In situation where the detection channel section is essentially free of biochemical components un-dissolved biochemical components do not interfere with and optionally complicate the optical detection.

The optical property or properties detected may in principle be any optical property of the fluid sample which is affected by the observed reaction. Unless other how specified the optical property should be interpreted to include a combination of two or more optical properties. As examples of optical properties can be mentioned absorption, transmission, reflecting and/or scattering.

In one embodiment the optical detector is arranged to transmit light onto the aperture section and to detect a light transmission from the aperture section, wherein the light transmission from the aperture section being selected from light transmitted through the sample, reflectance scattering of light, transmittance scattering of light and any combinations thereof.

In one embodiment the optical detector comprises at least one light emitter directing light towards the aperture section.

The light emitter may in principle be any kind of light emitter capable of emitting a sufficient amount of light for performing the detection. The light emitter may for example be selected from the group of a LED (Light Emitting Diode), a laser, an electroluminescent device, an incandescent lamp and a neon light.

The light emitter may preferably be arranged to emit a light comprising wavelength of about 600 nm or less, preferably at least about 50%, such as at least about 60%, such as at least about 70%, such as at least about 80% of the light intensity being electromagnetic waves with a wavelength of about 600 nm or less.

In one embodiment the light emitter is arranged to emit a light comprising wavelength of about 450 nm or less, preferably at least about 50%, such as at least about 60%, such as at least about 70%, such as at least about 80% of the light intensity being electromagnetic waves with a wavelength of about 450 nm or less.

The light intensity of electromagnetic waves of certain wavelengths is determined as the intensity of said wavelength incident on the first surface of the microfluidic device. The intensity is measured in watts per square meter ($W \cdot m^{-2}$).

Preferred light emitters includes light emitter emitting light with wavelength in the intervals from about 200 to about 600 nm, preferably from about 300 to 500 nm, such as from about 380 to about 460 nm, such as from about 410 to about 440 and in particular in the range from about 425 to about 440 nm when the fluid sample or at least about 15% thereof, such as the major part by volume thereof is whole blood.

In one embodiment the light emitter is arranged to emit a light having one or more wavelengths selected such that the major part of the light such as at least about 60%, such as at least about 70%, such as at least about 80% is absorbed by non-coagulated whole blood.

In one embodiment light emitter is arranged to emit a light having one or more wavelengths selected such that the major part of the light such as at least about 60%, such as at least about 70%, such as at least about 80% is absorbed by coagulated whole blood.

The optical detector may be any kind of optical detector capable of detecting the selected optical property which is to be determined as a function of time.

In one embodiment the optical detector is selected from fluorescence polarization detectors, fluorescence fluctuation detectors, light absorption sensors, and light scattering sensors. When fluorescence detectors are used the fluid sample should preferably comprise a fluorescence component.

Examples of useful polarization detectors are for example disclosed in WO 99/64840. Examples of useful concentration detection sensors are for example disclosed in U.S. Pat. No. 5,569,608. Examples of particle counting sensors are for example disclosed in US 2004/0011975 and WO 2004/042402 (using scattered light).

In one embodiment the optical detector comprises at least one light detector, said light detector preferably being selected from a photo sensor such as a photo-multiplier tube (PMT), an avalanche photodiode (ADP), a Silicon Photodiode or a charge coupled device (CCD).

In one embodiment the light detector being arranged in relation to the microfluidic device to detect light transmission from the aperture section, the light transmission from the aperture section preferably being selected from light transmitted through the sample, reflectance scattering of light, transmittance scattering of light and a combination thereof.

The optical detector may comprise two or more light detectors. In one embodiment the optical detector comprises a plurality of light detectors in the form of a CCD-array for example arranged to collect signal from a plurality of apertures of the same microfluid device.

The light detector may be arranged to detect light with one or more wavelength as emitted by the emitter. In one embodiment the microfluidic system comprises an optical element placed in the light path from the emitter to the light detector, which optical element such as an optical filter or a optical modifier which modifies all or part of the passing light.

In one embodiment the microfluidic system comprises a microfluidic device holder for fixing the microfluidic device in a desired position in relation to the optical detector, optionally the microfluidic device holder being an integrated part of the optical detector. By this arrangement a more stable system can be obtained.

The microfluidic system may preferably further comprise a computer element arranged to perform calculation based on measurements obtained from the optical detector. The computer element may preferably being arranged to determining the optical property of said aperture section as a function of time, more preferably to determine change of absorbance of the aperture section and thereby the detection channel section as a function of time. If the system comprises an external pressure/suction source this pressure/suction source should preferably be digitally connected to the computer element so that the applied pressure/suction can be used in the calculations performed by the computer.

In order to calibrated the system one or more tests using one or more fluid sample(s) with known composition(s) may be performed as reference(s) In one embodiment the microfluidic system is a system for performing a coagulation test on blood. The detection channel section of the flow channel has capillary dimensions for a biological sample comprising at least 90% by volume of whole blood, the flow channel comprises at least one reaction chamber placed upstream to the detection channel section and the optical detector comprises a light emitter arranged to emit a light which is essentially equal absorbable by whole blood in non-coagulated state and whole blood in coagulated state.

In one embodiment the microfluidic system is a system for performing an agglutination test. The detection channel section of the flow channel comprises at least one hindrance element for slowing down the velocity of the flow front of a fluid sample in said test channel as the fluid sample is agglutinating. The hindrance element may for example be in the form of a decrease in channel cross-sectional area, in the form of one or more abrupt curves in the channel, in the form of elements protruding from the channel walls, in the form of a secondary element inserted into the upper test channel section or in the form of combinations of the above mentioned hindrance elements.

The invention also relates to a method for performing a test on a fluid sample to determine a change in the sample The method of the invention comprises
providing a planar microfluidic device having a first and a second opposite surfaces and comprising a flow channel with an inlet and a detection channel section having a length;
providing an optical detector comprising a light emitter and a light detector;
arranging the optical detector to be in optical communication with an aperture section comprising at least a part of said detection channel section and a transparent window into said detection channel section;

applying the fluid sample in the inlet and allowing it to flow into the detection channel section:

observing an optical property of the aperture section as a function of time, and determining if a change in the fluid sample has occurred.

The method of the invention may be performed using the microfluidic system as described above. Furthermore in embodiments of the method the various parameters of may be as described above.

In one embodiment the method of the invention further comprises determining when a change in the fluid sample has occurred. This can e.g. be performed by determining the time frame from exposing the fluid sample to a reagent e.g. determined using a position indicator as described above and until an optical change and/or pressure/suction change is detected which change is related to the change of fluid sample.

In one embodiment the method of the invention further comprises determining to which degree a change in the fluid sample has occurred. This can e.g. be performed by determining the degree of an optical change and/or pressure/suction change at a specific point in time where the change of the fluid sample has been determined to have occurred.

In one embodiment the method comprising applying a pressure and/or a suction force to the fluid sample to drive the sample into the detection channel section so that a flow front of the fluid sample is progressing along the detection channel section, preferably at a desired velocity. It is desired that the pressure/suction applied is determined (the pressure/suction source may be digitally connected to the optical device e.g. via a computer) for using in calculation. However a simple manually operated pump may also be used.

In one embodiment the method comprises applying an essentially constant pressure and/or an essentially constant suction to the fluid sample.

In one embodiment the method comprises applying a gradually increasing pressure and/or a gradually increasing suction to the fluid sample.

In one embodiment the method comprises applying a pressure and/or a suction to the fluid sample to drive the front of the fluid sample along the detection channel section with a predetermined velocity, the pressure and/or suction applied being used to determine if, when and/or to which degree a change in the fluid sample has occurred.

In principle the fluid sample may be any kind of sample which sample is changing at least one optical property or at least one flow property when subjected to a reagent. Preferably the fluid sample is a sample which is changing at least one flow property, such a viscosity when subjected to a reagent.

The method of the invention is particular useful for a fluid biological comprising at least about 10% by volume of biological fluid, such as at least about 40% by volume, such as at least about 50% by volume, such as at least about 75% by volume of biological fluid, the remaining part of the biological sample preferably being selected from water, physiologically aqueous solution and reagent for the biological fluid.

In a preferred embodiment the fluid sample is or comprises a biological fluid selected from the group of blood fractions, whole blood, urine and saliva. More preferably the fluid sample is a biological sample comprising at least about 90% by volume of whole blood.

In one embodiment a reagent is added to the fluid sample prior to the fluid sample is entering the detection channel section, the reagent preferably being selected from a coagulation promoting reagent, such as thromboplastin, chemical lysing agents and an agglutination reagent, such as Anti citrate and an agglutination reagent, such as Anti-A antisera, Anti-B antisera and latex microspheres with attached antibodies.

In one embodiment heat is applied to perform a reaction of the blood either alone or in combination with one or more reagents.

In one embodiment where the flow channel comprises at least one reaction chamber placed upstream to the detection channel section, the method comprises applying a reagent for the sample in said reaction chamber, the reagent preferably being selected from a coagulation promoting reagent and an agglutination reagent.

In one embodiment the reagent being applied via a secondary inlet to the reaction chamber.

In one embodiment the flow channel comprises at least one reaction chamber placed upstream to the detection channel section, the reaction chamber comprises a reagent for the sample, the reagent preferably being selected from a coagulation promoting reagent and an agglutination reagent.

In one embodiment the flow channel comprises at least one reaction chamber placed in the detection channel section, the method comprises applying a reagent for the sample in said reaction chamber, the reaction chamber comprises a reagent for the sample, the reagent preferably being selected from a coagulation promoting reagent and an agglutination reagent.

In one embodiment the flow channel comprises at least one reaction chamber with a reagent placed in the detection channel section, and a position indicator immediately adjacent to the reaction chamber, the method comprising adjusting the flow of the fluid sample such that the fluid sample has a predetermined time to react with the reagent. For example, when the flow front of the liquid sample reaches the position indicator an optical change is observed (or a pressure/suction signal if pressure/suction applied from an external source is adjusted to keep the optical property at predetermined level), the pressure/suction applied may thereafter be adjusted such that the fluid sample has a predetermined time to react with the reagent.

In one embodiment where the flow channel comprises at least two detection channel sections placed with a distance from each other (e.g. 10 mm or more, such as 50 to 500 mm in distance), an in flow direction first detection channel section comprising a reaction chamber and a second detection channel section, the method comprising detecting when the fluid sample reaches the reaction chamber and determining if, when and/or to which degree a change in the fluid sample has occurred in the second detection channel section.

The second detection channel section preferably being longer than the first detection channel section.

In one embodiment the flow channel comprises a position indicator immediately adjacent to a part of the flow channel which is upstream to the aperture section, the method comprising determining the point in time where the fluid sample enters the detection channel section.

In one embodiment the flow channel comprises a position indicator immediately adjacent to a part of the flow channel which is downstream to the aperture section, the method comprising determining if and optionally the point in time where the fluid sample exits the detection channel section.

The light emitter may preferably be arranged to emit a light comprising wavelength as described above.

In one embodiment the microfluidic device is held in a fixed position in relation to the optical detector during the detection.

The light detector may preferably be connected to a computer element arranged to perform calculation based on measurements obtained from the optical detector, the method comprises determining an optical property as a function of time, such as determining the change of absorbance of the aperture section.

In one embodiment the method comprising calculating the slope as a function of time of the change of absorbance versus time curve using the computer element. In dependence of the aperture sections(s) and the detection channel section(s) different determinations can be obtained by calculating the slope. The calculated slope can for example be a determination of the flow velocity which will normally be useful in the determination of viscosity of the sample. If the sample is blood the slope can for example be used to determine the hematocrit volume fraction. The hematocrit volume fraction (Ht or HCT) (also called or packed cell volume (PCV) or erythrocyte volume fraction (EVF)) is the proportion of blood volume that is occupied by red blood cells concentration.

In one embodiment the method of the invention is a method for performing a coagulation test on blood wherein the light detector being arranged in relation to the microfluidic device to detect light transmission from the detection channel section, the light transmission from the detection channel section being selected from light transmitted through the sample, reflectance scattering of light, transmittance scattering of light and a combination thereof, the method comprising introducing the blood sample into the detection channel section of the flow channel and observing the change of light detected by the light detector as a function of time, and determining if coagulation in the fluid sample has occurred.

In one embodiment of the method of the invention for performing a coagulation test on blood the method further comprises determining of the time and/or degree of coagulation.

In one embodiment of the method of the invention for performing a coagulation test on blood, the flow channel comprises at least one reaction chamber placed upstream to the detection channel section and the optical detector comprises a light emitter arranged to emit a light which is essentially equally absorbable by whole blood in non-coagulated state and whole blood in coagulated state.

In one embodiment the method of the invention is a method for performing an agglutination test wherein the detection channel section of the flow channel comprises at least one a hindrance element for slowing down the velocity of the flow front of a fluid sample in said test channel as the fluid sample is agglutinating, said hindrance elements preferably being, in the form of a decrease in channel cross-sectional area, in the form of one or more abrupt curves in the channel, in the form of one or more elements protruding from the channel walls and/or in the form of a one or more secondary elements inserted into the upper test channel section.

In one embodiment of the method for performing an agglutination test, the method comprising adding an agglutination reagent to the fluid sample prior to the fluid sample is entering the detection channel section or in the detection channel section, the reagent preferably being selected from Anti-A antisera, Anti-B antisera and latex microspheres with attached antibodies.

In one embodiment of the method for performing an agglutination test, the light detector being arranged in relation to the microfluidic device to detect light transmission from the detection channel section, the light transmission from the detection channel section being selected from light transmitted through the sample, reflectance scattering of light, transmittance scattering of light and a combination thereof, the method comprising introducing the fluid sample into the detection channel section of the flow channel and observing the change of light detected by the light detector as a function of time, and determining if agglutination in the fluid sample has occurred.

In one embodiment of the method for performing an agglutination test, the method further comprises determining the time and/or degree of agglutination.

BRIEF DESCRIPTION OF DRAWINGS

Examples of embodiments of the invention will be described below with reference to the drawings where.

Figure 1A:
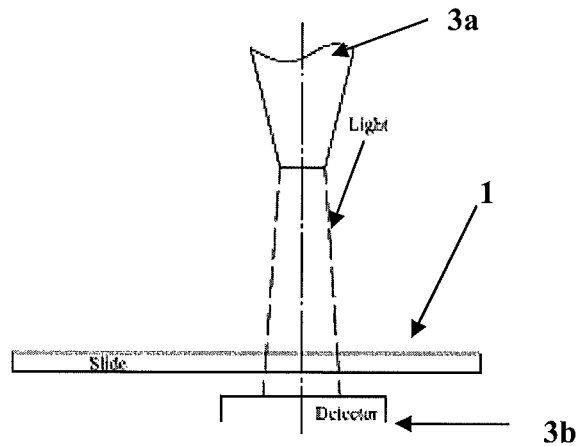
FIG. 1 is a schematic side view of a first microfluidic system of the invention.
Figure 4:
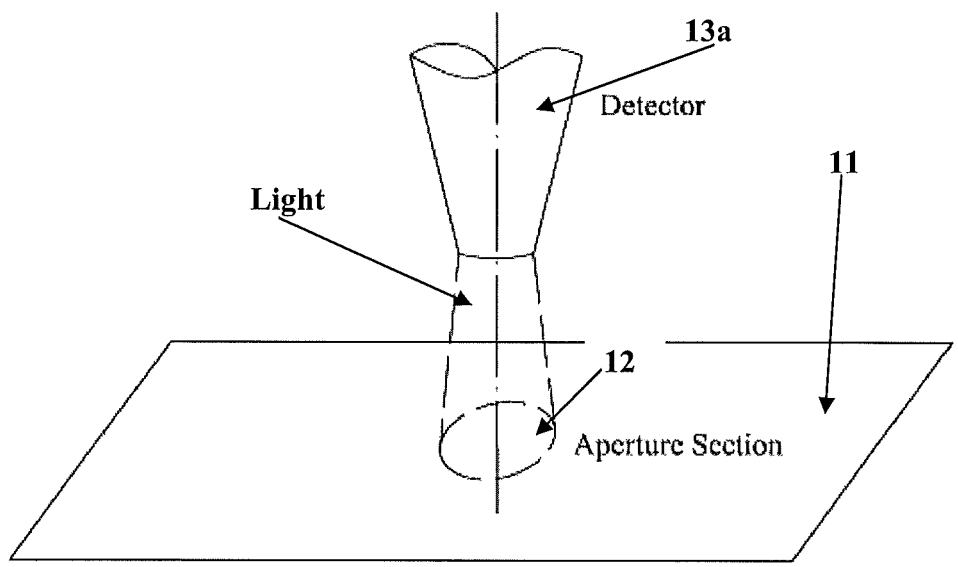
FIG. 4 is a schematic perspective side view of the microfluidic system of FIG. 1.

The microfluidic system shown in FIGS. 1 and 4 comprises a microfluidic device 1 having a first and a second opposite surfaces and an optical detector 3a, 3b comprising a light emitter 3a and a light detector 3b. The first surface of the microfluidic device 1 is the surface closest to the light emitter and the second surface of the microfluidic device 1 is the surface opposite to the first surface. The light emitter 3a and the light detector 3b are placed on opposite sides of the microfluidic device 1, so that light emitted from the light emitter 3a is transmitted onto an at least partly transparent section of the microfluidic device 1, and the light that passes through this transparent section is collected by the light detector 3b. This transparent section onto which the light is emitted is called the aperture section 2. In this aperture section of the microfluidic device 1, the microfluidic device 1 comprises a not shown detection channel section. The microfluidic device 1 is here in the form of a slide which is transparent at least in a section comprising the aperture section 2.

In use the light emitter 3a is turned on to transmit a light beam towards the aperture section 2 and the and the light detector 3b collects the light that is transmitted through the aperture section 2 of the microfluidic device 1. A sample is applied to flow into the detection channel section. As the sample passes into the detection channel section and fill it more and more, the amount of light transmitted decreases accordingly. The flow velocity of the sample as a function of time can thereby be determined. Depending on the wavelength or wavelengths of light emitted from the light emitter and received by the light receiver other parameters may also be determined, such a coagulation or agglutination degrees. It should here be understood that the light detector any be arranged to detect scattered light as well as simply transmitted light.

Figure 2:
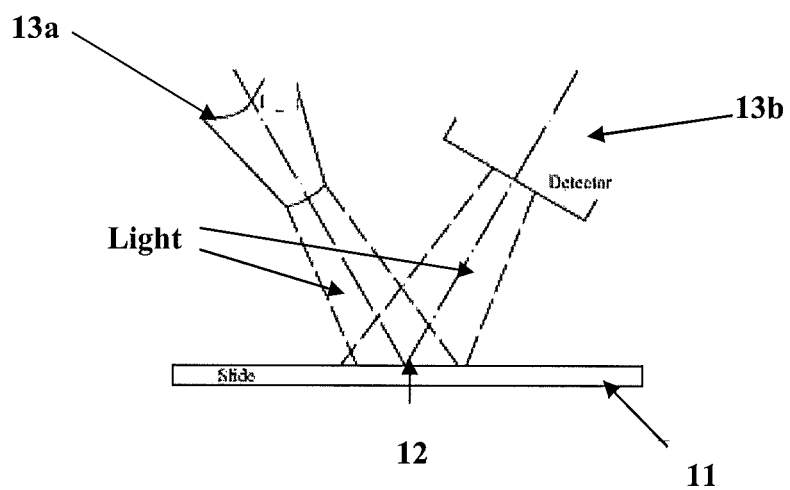
FIG. 2 is a schematic side view of a second microfluidic system of the invention.

The microfluidic system shown in FIG. 2 correspond in principle to the microfluidic system shown in FIGS. 1 and 4, with the difference that the light detector detects reflected light e.g. including or reflected scattered light. The microfluidic system shown in FIG. 2 comprises a microfluidic device 11 having a first and a second opposite surfaces and an optical detector 13a, 13b comprising a light emitter 13a and a light detector 13b. The first surface of the microfluidic device 11 is the surface closest to the light emitter 13a and the light detector 13b and the second surface of the microfluidic device 11 is the surface opposite to the first surface. The light emitter 13a and the light detector 13b are placed on same sides of the microfluidic device 11, so that light emitted from the light emitter 13a is transmitted onto an at least partly transparent section of the microfluidic device 11, and the light that is reflected from this transparent section is collected by the light detector 13b. This at least partly transparent section onto which the light is emitted is called the aperture section 12. In this aperture section 12 of the microfluidic device 11, the microfluidic device 11 comprises a not shown detection channel section. In this embodiment the aperture section 12 may be essentially transparent when the detection channel section is empty or it may be less transparent, but at least its first surface should be transparent to expose the detection channel section. The microfluidic device 11 is here in the form of a slide which is transparent at least in a section comprising the aperture section 12.

In use the light emitter 13a is turned on to transmit a light beam towards the aperture section 12 and the and the light detector 13b collects the light—if any—that is reflected from the aperture section 12 of the microfluidic device 11. A sample is applied to flow into the detection channel section. As the sample passes into the detection channel section and fill it more and more, the amount or wavelength profile of light reflected changes accordingly, for example the amount of light may increase. The flow velocity of the sample as a function of time can thereby be determined. Depending on the wavelength or wavelengths of light emitted from the light emitter and received by the light receiver other parameters may also be determined, such a coagulation or agglutination degrees.

Figure 3:
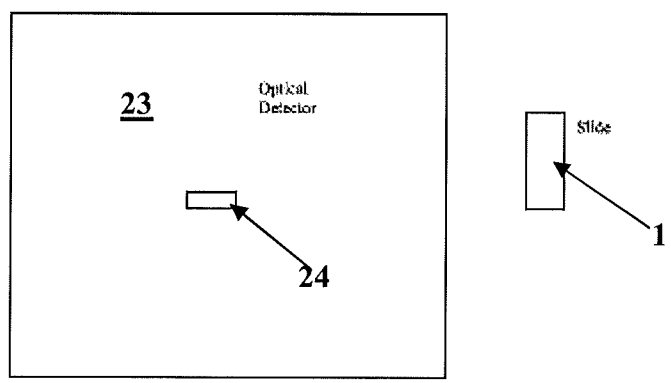
FIG. 3 shows in schematic form an optical detector and a microfluidic device.

FIG. 3 shows in schematic form an optical detector 23 and a microfluidic device 1. The optical detector 23 is shown as a box with a slit 24 into which the microfluidic device 1, can be inserted. The optical detector 23 comprises not shown light emitter and light detector. The optical detector 23 may further comprise or be connected to a computer element which may be arranged to be used e.g. for calibrating the system and for determining the optical property of the aperture section and based on this calculate one or more properties of the sample. The show optical detector 23 is adapted for manual use, but the skilled person will understand that the optical detector could be arranged to be semi or fully automated.

Figure 5:
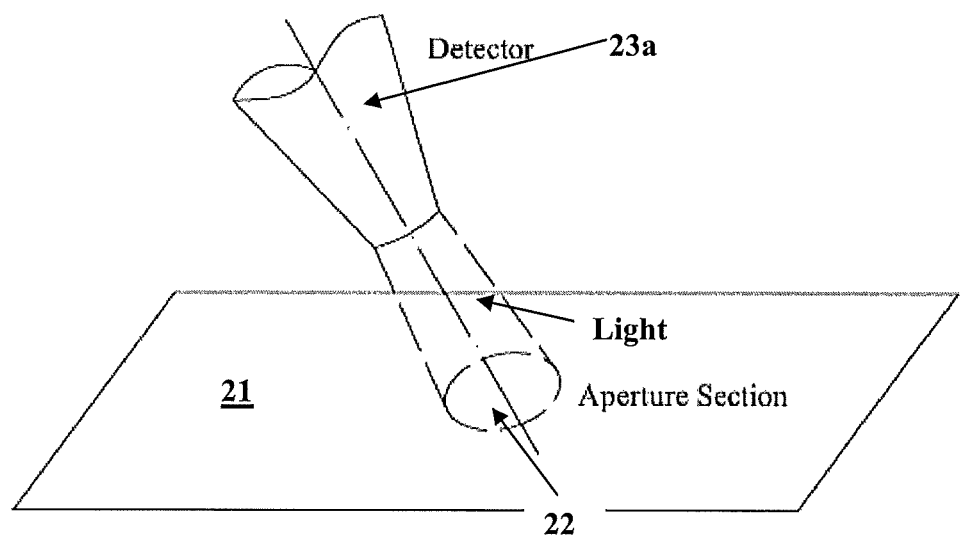
FIG. 5 is a schematic perspective side view of a microfluidic system corresponding to the microfluidic system shown in FIGS. 1 and 4.

The microfluidic system shown in FIG. 5 correspond to the system shown in FIG. 4 with the difference that the light emitter 23a is transmitting the light beam towards the aperture section 22 with an angle to the first surface of the slide 21. The not shown light receiver may be placed at the same side as the light emitter 23a to collect reflected light and/or the light receiver may be placed on the opposite side of the microfluidic device 21 to collect light transmitted through the aperture section.

Figure 6:
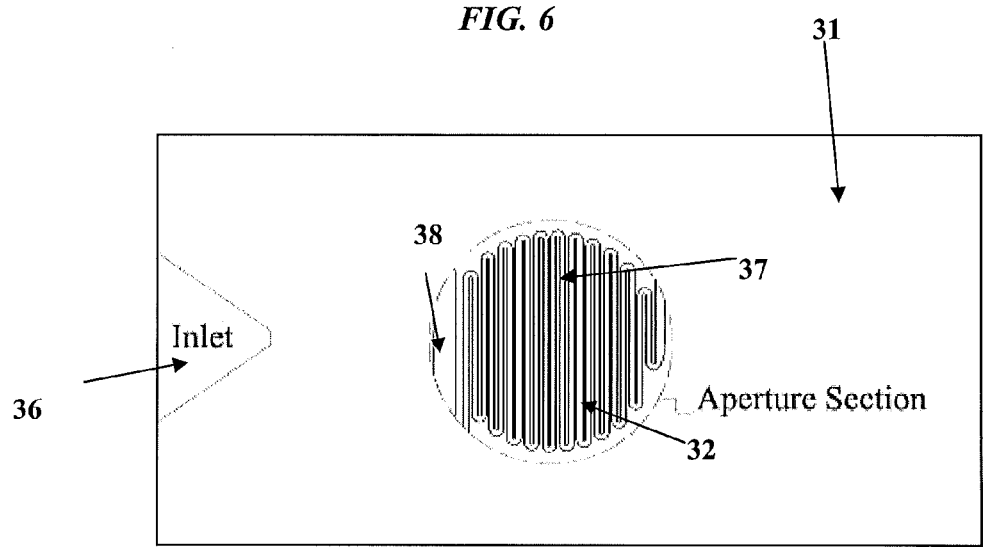
FIG. 6 is a schematic top view of a microfluidic device of the microfluidic system.

FIG. 6 is a schematic top view of a microfluidic device 31 of the microfluidic system. The microfluidic device 31 comprises an inlet 36 and a flow channel comprising a meander shaped detection channel section 37, and an aperture section 32 comprising said detection channel section 37 and a transparent window into said detection channel section. The flow channel further comprises a position indicator 38. The flow channel provides a flow path from the inlet 36 to the position indicator 38 in the aperture section 32, out of the aperture section 32 and into the detection channel section 37 in the aperture section, and from the detection channel section 37 to a section where air can escape from the flow channel. The flow channel may comprise one or more not shown reaction chambers. When a sample is introduced into the inlet 36, it will flow to the position indicator 38, which here is a flow section with a relatively large width, which will provide a relatively large optical signal to indicate that the sample is about to flow into the detection channel section 37. Relatively soon after the position indicator 38 has been filled, the sample will flow into the position indicator 38 where the velocity as a function of time as well as other properties can be determined as described above.

Figure 7A:
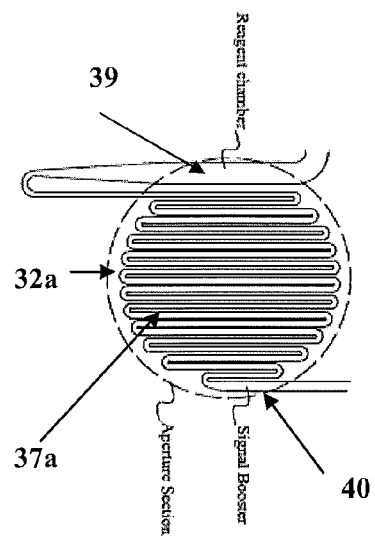
FIGS. 7a, 7b and 7c are variations of the microfluidic device shown I FIG. 6.
Figure 7B:
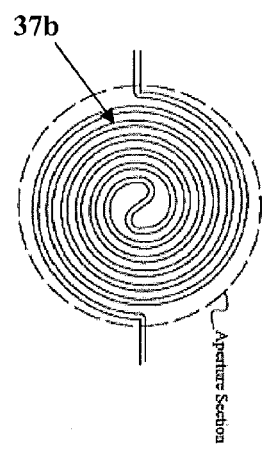
Figure 7C:
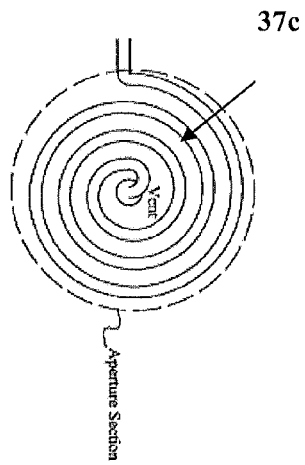

FIGS. 7a, 7b and 7c are variations of the microfluidic device shown I FIG. 6. In these figures only the aperture parts and a part of the flow channel adjacent to the aperture parts of the slides are shown.

In the microfluidic device shown in FIG. 7a the flow channel comprises a reaction chamber 39 which is at least partly placed in the aperture section 32a. The detection channel section 37a is meander shaped and comprises a signal booster section 40 which is a position indicator in the form of a section of the detection channel section 37a which has a larger width and thereby provides a larger optical signal.

In the microfluid device shown in FIG. 7b the detection channel section 37b is coiled as a double coil. In the microfluid device shown in FIG. 7c the detection channel section 37c is coiled as a single coil with the vent for the escape of air placed central in the coil. The skilled person will know that the shape of the flow channel and the detection channel section may be varied as desired.

Figure 8:
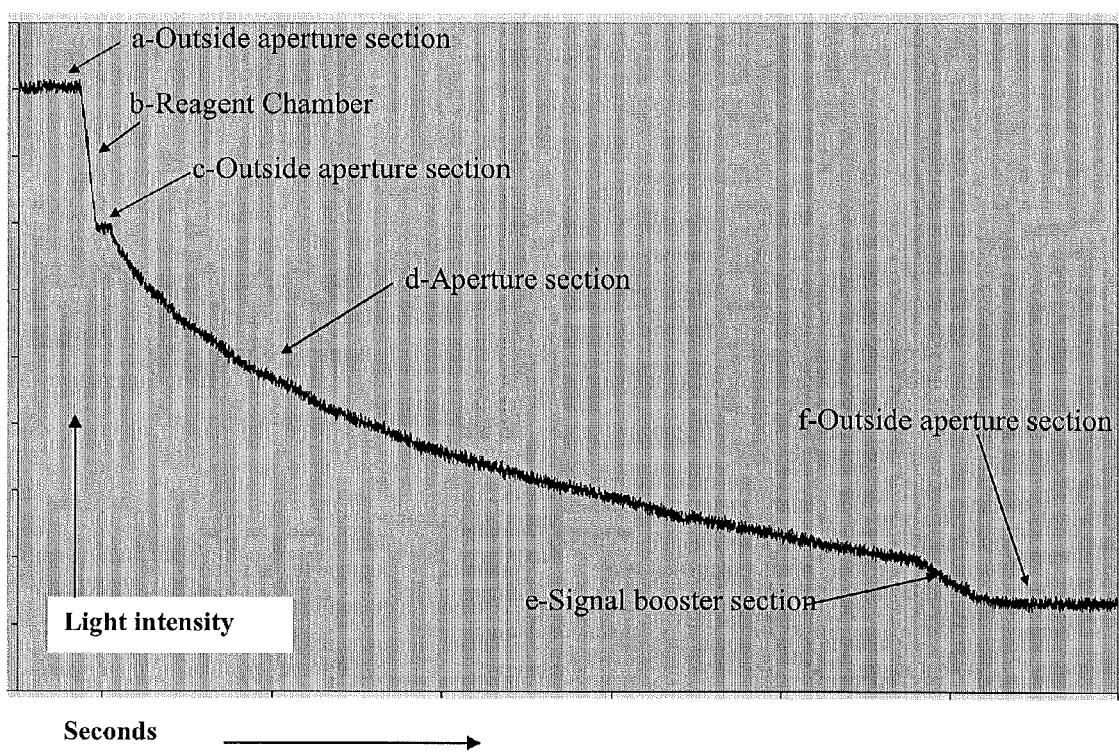
FIG. 8 show the light signal received over time measured using a microfluidic system of the invention.

FIG. 8 show the light signal received over time measured using a microfluidic system of the invention. The microfluidic system of the invention used is a system as shown in FIGS. 1 and 4 using a microfluidic device as shown in FIG. 7a where the collected light signal decreases over time as the sample is filling up the detection channel sections. Initially at point a) the light detector collect maximum amount of light because the sample has not yet entered the aperture section. When the sample reaches the reagent chamber 39 at point b), the light signal (also called light intensity) decreases drastically. The reaction chamber 39 accordingly also functions as a position indicator. At point c) it can be seen that the decrease in light signal temporarily stops, which indicate that the reagent chamber is filled with sample and the flow front of the sample for a short while is outside the aperture section. As the light signal again starts to decrease the sample flow front has entered the detection channel section 37a and in point d) it is seen that the decrease in light intensity continues as the sample fills up the detection channel section 37a. When the flow front of the sample reaches the signal booster section 40 in point e), a boosted decrease in light signal is detected, and there after the flow front will exit the detection channel section 37a as seen in point f).

Figure 9:
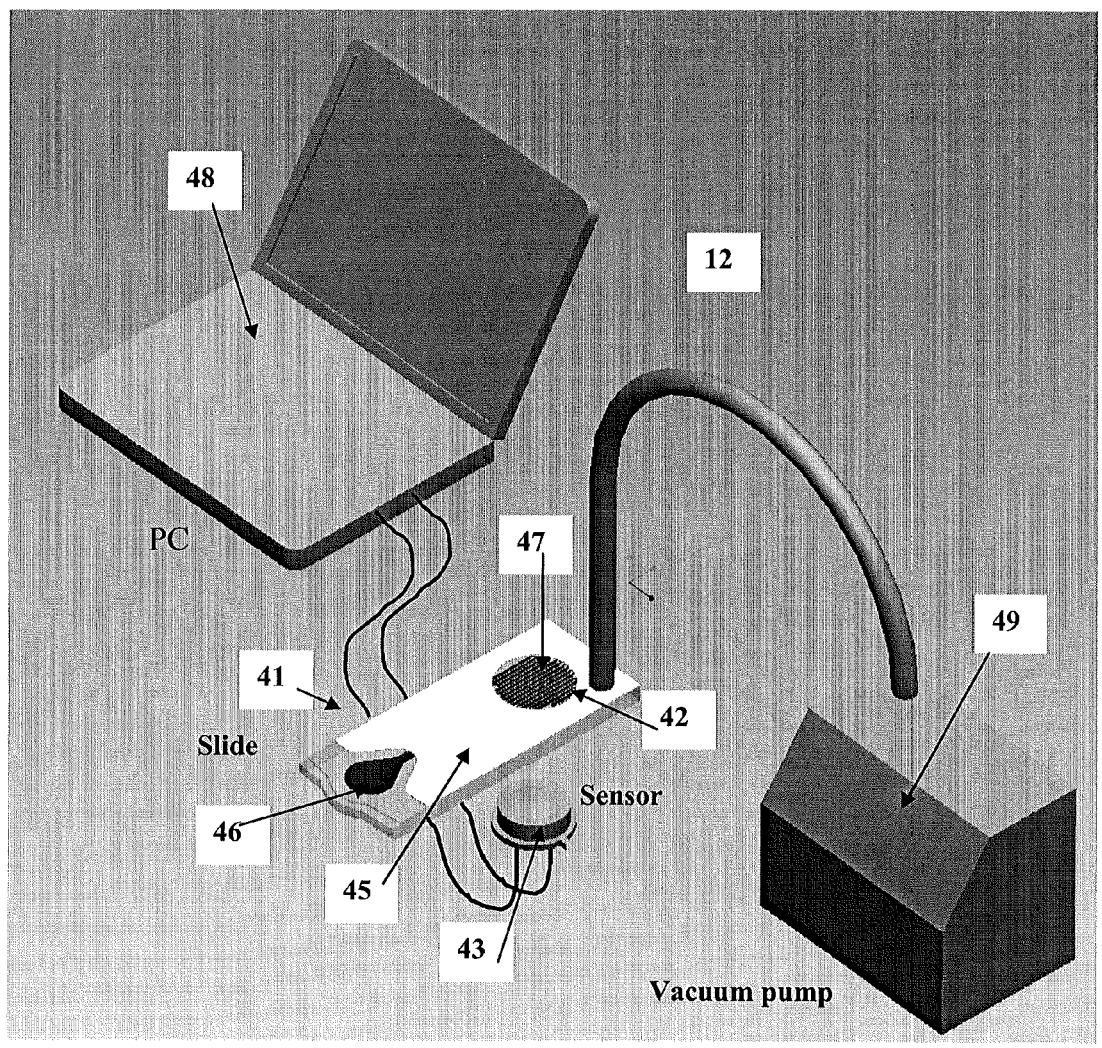
FIG. 9 is a schematic perspective view of a third microfluidic system of the invention.

FIG. 9 is a schematic perspective view of a third microfluidic system of the invention. The microfluidic system comprises a microfluidic device 41 and a partly shown optical detector 43. The microfluidic device 41 comprises a flow channel with a detection channel section 47. The microfluidic device comprises an aperture section 42 comprising said detection channel section 47 and a transparent window into said detection channel section. In the microfluidic system shown in FIG. 9 only the light detector 43 of the optical detector 43 is shown. The optical detector 43 also comprises a not shown light emitter arranged to transmit light onto the aperture section 42 of the microfluidic device 41. The microfluidic device 41 comprises an inlet 46 to a flow channel which leads to the detection channel section 47 as described above. To reduce the amount of false signal the area of the microfluidic device 41 outside the aperture section 42 has been covered by a non transparent cover 45. The microfluidic device is connected to a vacuum pump for driving the sample through the flow channel. The optical detector 43 is connected to a PC 48 which is used to collect and perform calculation on the light signal collected. The PC 48 may further be used to control the vacuum pump and use the resulting vacuum applied in the calculation relating to properties of the sample. The system may e.g. be regulated such that the vacuum is adjusted to obtain a desired velocity/direction (back flow)/time profile.

The figures are schematic and simplified for clarity, and they just show details which are essential to the understanding of the invention, while other details are left out. Throughout, the same reference numerals are used for identical or corresponding parts.

Further scope of applicability of the present invention will become apparent from the detailed description given above. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A microfluidic system comprising:
   a microfluidic device comprising:
   a first surface,
   a second opposite surface,
   a light emitter,
   an optical detector,
   a flow channel with a single inlet for feeding a fluid sample, a detection channel section downstream of the single inlet, the detection channel section having a length of at least about 1 mm, one aperture section comprising at least a part of said detection channel section and a transparent window covering said one aperture section,
   the detection flow channel includes a continuous length that is curved in at least some regions such that the detection flow channel has a plurality of sections that extend parallel or adjacent one another within the aperture section,
   wherein the light emitter is configured to direct light toward the aperture section, and
   the optical detector is arranged to be in optical communication with said aperture section and is programmed to determine changes of absorbance of an entirety of the aperture section during a period of time in which the same fluid sample is filling the detection channel section in said aperture section as a function of time.

2. A microfluidic system as claimed in claim 1 wherein the flow channel comprises two or more detection channel sections arranged wholly or partly in said aperture section.

3. A microfluidic system as claimed in claim 1 wherein the device comprises a transparent window into said flow channel beyond the detection channel section.

4. A microfluidic system as claimed in claim 1 wherein the aperture section comprises at least a part of said detection channel section and an aperture area beyond said detection channel section, the aperture area beyond said detection channel section being transparent, or essentially non-transparent, such as absorbing and/or reflecting light from said optical detector.

5. A microfluidic system as claimed in claim 1 wherein the aperture section or the aperture sections in total cover the major part of the detection channel section, and the aperture section or the aperture sections in total cover a size of at least about 10 µm².

6. A microfluidic system as claimed in claim 1 wherein at least the detection channel section of the flow channel has dimensions to permit capillary action for a biological sample comprising a biological fluid selected from the group of blood fractions, whole blood, urine and saliva.

7. A microfluidic system as claimed in claim 1 wherein the detection channel section has a cross-sectional channel width parallel to the first surface, the detection channel section comprises at least one position indicator provided by a change of the cross-sectional channel width of at least about 25% within a length of channel of about 5 mm.

8. A microfluidic system as claimed in claim 7 wherein the detection channel section comprises one or more protruding elements along at least a part of said position indicator.

9. A microfluidic system as claimed in claim 7 wherein the detection channel section comprises a position indicator immediately adjacent to a part of the flow channel which is upstream to or downstream to the aperture section.

10. A microfluidic system as claimed in claim 7 wherein the detection channel section comprises a position indicator immediately adjacent to a reaction chamber.

11. A microfluidic system as claimed in claim 1 wherein the flow channel comprises at least one reaction chamber placed upstream to the detection channel section, or in the detection channel section.

12. A microfluidic system as claimed in claim 1 wherein the detection channel section comprises a reaction chamber with a reagent, the reagent in non dissolved condition has an optical property which differs when the reagent is dissolved.

13. A microfluidic system as claimed in claim 12 wherein the reaction chamber comprises an agglutination reagent or a coagulation reagent for a fluid sample.

14. A microfluidic system as claimed in claim 1 wherein the optical detector is arranged to transmit light onto the entirety of the aperture section and to detect changes of an optical property from the entirety of the aperture section.

15. A microfluidic system as claimed in claim 1 wherein the optical property being selected from absorption, transmission, reflecting and/or scattering.

16. A microfluidic system as claimed in claim 1 wherein the light emitter is arranged to emit a light comprising wavelength of about 600 nm or less.

17. A microfluidic system as claimed in claim 1 wherein the light emitter is arranged to emit a light comprising wavelength of about 450 nm or less.

18. A microfluidic system as claimed in claim 1 wherein the light emitter is arranged to emit a light having one or more wavelengths selected such that the major part of the light is absorbed by non-coagulated whole blood.

19. A microfluidic system as claimed in claim 1 wherein the light emitter is arranged to emit a light having one or more wavelengths selected such that the major part of the light is absorbed by coagulated whole blood.

20. A microfluidic system as claimed in claim 1 wherein the microfluidic system comprises a microfluidic device holder for fixing the microfluidic device in a desired position in relation to the optical detector.

21. A microfluidic system as claimed in claim 1 wherein the microfluidic system further comprises a computer arranged to perform calculations based on measurements obtained from the optical detector, the computer being arranged to determine an optical property of said one or more aperture sections as a function of time.

22. A microfluidic system for performing an agglutination test as claimed in claim 1 wherein the detection channel section of the flow channel comprises at least one hindrance element for slowing down the velocity of the flow front of a fluid sample in said test channel as the fluid sample is agglutinating, said hindrance elements being, in the form of at least one of a) a decrease in channel cross-sectional area, b) one or more abrupt curves in the channel, c) one or more elements protruding from the channel walls and d) one or more secondary elements inserted into the upper test channel section.

23. A microfluidic system as claimed in claim 2 wherein at least one of said detection channel sections is at least about 25% longer than the one or more other detection channel sections.

24. A microfluidic system as claimed in claim 1 wherein the changes of absorbance represents a velocity of the same fluid sample.

25. A microfluidic system as claimed in claim 1 wherein the flow channel includes:
a first section at a region where the flow channel first enters the aperture section;
a second section that is downstream of the first section and which is located outside of the aperture section; and
a third section that is downstream of the second section and which is located within the aperture section.

26. A method of performing a test on a fluid sample to determine a change in the sample comprising
providing a planar microfluidic device having a first surface and a second opposite surface and comprising a flow channel with an inlet and a detection channel section having a length;
providing an optical detector comprising a light emitter and a light detector;
arranging the optical detector to be in optical communication with an aperture section comprising at least a part of said detection channel section and a transparent window into said detection channel section;
applying the fluid sample in the inlet and allowing it to flow into the detection channel section;
observing an optical property of the fluid sample in the aperture section as a function of time, and
determining if a change in the fluid sample has occurred;
wherein the method is performed using a microfluidic system as claimed in claim 1.

27. A method as claimed in claim 26 wherein the method further comprising determining when a change in the fluid sample has occurred.

28. A method as claimed in claim 26 wherein the method further comprising determining to which degree a change in the fluid sample has occurred.

29. A method as claimed in claim 26 wherein the method comprising applying a pressure and/or a suction to the fluid sample to drive the sample into the detection channel section so that a flow front of the fluid sample is progressing along the detection channel section, preferably at a desired velocity.

30. A method as claimed in claim 29 wherein the method comprising applying a pressure and/or a suction to the fluid sample to drive the front of the fluid sample along the detection channel section with a predetermined velocity, the pressure and/or suction applied being used to determine if, when and/or to which degree a change in the fluid sample has occurred.

31. A method as claimed in claim 26 wherein the fluid sample is a biological sample comprising at least about 10% by volume of biological fluid.

32. A method as claimed in claim 26 wherein the fluid sample is a biological sample comprising a biological fluid selected from the group of blood fractions, whole blood, urine and saliva.

33. A method as claimed in claim 26 wherein a reagent is added to the fluid sample prior to the fluid sample is entering the detection channel section, the reagent being selected from a coagulation promoting reagent, such as thromboplastin and chemical lysing agents and an agglutination reagent, such as Anti-A antisera, Anti-B antisera and latex microspheres with attached antibodies.

34. A method as claimed in claim 26 wherein the flow channel comprises at least one reaction chamber placed upstream to the detection channel section or in the detection channel section, the method comprises applying a reagent for the sample in said reaction chamber, the reagent being selected from a coagulation promoting reagent and an agglutination reagent.

35. A method as claimed in claim 26 wherein the flow channel comprises at least one reaction chamber placed in the detection channel section, the method comprises applying a reagent for the sample in said reaction chamber, the reaction chamber comprises a reagent for the sample, the reagent being selected from a coagulation promoting reagent and an agglutination reagent.

36. A method as claimed in claim 26 wherein the flow channel comprises at least two detection channel sections placed with a distance from each other, an in flow direction first detection channel section comprising a reaction chamber and a second detection channel section, the method comprising detecting when the fluid sample reaches the reaction chamber and determining if, when and/or to which degree a change in the fluid sample has occurred in the second detection channel section.

37. A method as claimed in claim 26 wherein the flow channel comprises a position indicator immediately adjacent to a part of the flow channel which is upstream to the aperture section, the method comprising determining the point in time where the fluid sample enters the detection channel section.

38. A method as claimed in claim 26 wherein the flow channel comprises a position indicator immediately adjacent to a part of the flow channel which is downstream to the aperture section, the method comprising determining if and optionally the point in time where the fluid sample exits the detection channel section.

39. A method as claimed in claim 26 wherein the microfluidic device is held in a fixed position in relation to the optical detector.

40. A method as claimed in claim 26 wherein the light detector being connected to a computer element arranged to perform calculation based on measurements obtained from the optical detector, the method comprises determining an optical property as a function of time.

41. A method as claimed in claim 26 for performing a coagulation test on blood wherein the light detector being arranged in relation to the microfluidic device to detect light transmission from the detection channel section, the light transmission from the detection channel section being selected from light transmitted through the sample, reflectance scattering of light, transmittance scattering of light and a combination thereof, the method comprising introducing the blood sample into the detection channel section of the flow channel and observing the change of light detected by the light detector as a function of time, and determining if coagulation in the fluid sample has occurred.

42. A method as claimed in claim 26 for performing a coagulation test on blood wherein the flow channel comprises at least one reaction chamber placed upstream to the detection channel section and the optical detector comprises a light emitter arranged to emit a light which is essentially equally absorbable by whole blood in non-coagulated state and whole blood in coagulated state.

43. A method as claimed in claim 26 for performing an agglutination test wherein the detection channel section of the flow channel comprises at least one a hindrance element for slowing down the velocity of the flow front of a fluid sample in said test channel as the fluid sample is agglutinating, said hindrance elements preferably being, in the form of at least one of a) a decrease in channel cross-sectional area, b) one or more abrupt curves in the channel, c) one or more elements protruding from the channel walls and d) one or more secondary elements inserted into the upper test channel section.

44. A method as claimed in claim 26 for performing an agglutination test wherein the light detector being arranged in relation to the microfluidic device to detect light transmission from the detection channel section, the light transmission from the detection channel section being selected from light transmitted through the sample, reflectance scattering of light, transmittance scattering of light and a combination thereof, the method comprising introducing the fluid sample into the detection channel section of the flow channel and observing the change of light detected by the light detector as a function of time, and determining if agglutination in the fluid sample has occurred.

* * * * *